(12) United States Patent
Chern Lin et al.

(10) Patent No.: US 7,306,610 B2
(45) Date of Patent: *Dec. 11, 2007

(54) METHOD AND DEVICE FOR FORMING A HARDENED CEMENT IN A BONE CAVITY

(75) Inventors: Jiin-Huey Chern Lin, Winnetka, IL (US); Chien-Ping Ju, Carbondale, IL (US)

(73) Assignee: Cana Lab Corporation, Taipei (TW)

( * ) Notice: Subject to any disclaimer, the term of this patent is extended or adjusted under 35 U.S.C. 154(b) by 683 days.

This patent is subject to a terminal disclaimer.

(21) Appl. No.: 10/393,044

(22) Filed: Mar. 21, 2003

(65) Prior Publication Data
US 2004/0186480 A1 Sep. 23, 2004

(51) Int. Cl.
A61F 2/00 (2006.01)

(52) U.S. Cl. .......................... 606/92; 606/94

(58) Field of Classification Search ................ 606/53, 606/86, 92, 93, 94; 623/23.62; 604/307, 604/344, 97.01, 103.07
See application file for complete search history.

(56) References Cited

U.S. PATENT DOCUMENTS

| | | | | | |
|---|---|---|---|---|---|
| 5,997,582 | A | * | 12/1999 | Weiss | 606/89 |
| 6,726,691 | B2 | * | 4/2004 | Osorio et al. | 606/94 |
| 2002/0058947 | A1 | * | 5/2002 | Hochschuler et al. | 606/94 |

* cited by examiner

*Primary Examiner*—Eduardo C. Robert
*Assistant Examiner*—James L. Swiger
(74) *Attorney, Agent, or Firm*—Bacon & Thomas, PLLC

(57) ABSTRACT

The present invention discloses a method of hardening a bone cement under an exerted pressure in a bone cavity including preparing a cement paste; injecting said cement paste into a balloon placed in a bone cavity; and allowing the cement paste harden in the balloon. Preferably, the balloon is opened after the cement paste is set, and the opened balloon is removed from the bone cavity. The present invention also discloses a device for use in the method of the present invention.

12 Claims, 2 Drawing Sheets

METHOD AND DEVICE FOR FORMING A HARDENED CEMENT IN A BONE CAVITY

FIELD OF THE INVENTION

The present invention is related to a technique of forming a set or hardened bone cement in bone cavity, and in particular to a technique of hardening a bone cement under an exerted pressure in a bone cavity.

BACKGROUND OF THE INVENTION

A calcium phosphate cement (abbreviated as CPC) has been widely used as an implant or filling material in dental and bone prosthesis, and its technical details can be found in many patents, for examples U.S. Pat. Nos. 4,959,104; 5,092,888; 5,180,426; 5,262,166; 5,336,264; 5,525,148; 5,053,212; 5,149,368; 5,342,441; 5,503,164; 5,542,973; 5,545,254; 5,695,729 and 5,814,681. Similar to CPC, calcium sulfate and bioactive glass have also been suggested or used as an implant or filling material in dental and bone prosthesis.

Heretofore the conventional method of forming a set or hardened bone cement in bone cavity involves directly injecting a cement paste into bone cavity, which suffers the followings drawbacks among others:
(1) Liquid/monomer can leak into surrounding tissue, nerve system, etc.;
(2) Dispersed cement particles in body fluid/blood, especially before being fully set, can penetrate into surrounding tissue through cancellous/porous bone;
   [Note: (1) and (2) can cause serious hazard during or after surgery]
(3) Without applying pressure, the strength of the cement is significantly low and easy to disperse/disintegrate.
   [Note: Surgeons usually don't apply pressure to the injected cement paste during/after injection thereof due to the above-mentioned (1) and (2) reasons]

SUMMARY OF THE INVENTION

A primary objective of the present invention is to provide a method and a device for forming a hardened cement in a bone cavity, which are free of the aforesaid prior art drawbacks.

The method disclosed in the present invention comprises the following steps:
a) preparing a cement paste;
b) injecting said cement paste into a pocket; and
c) allowing said cement paste harden in said pocket.

Preferably, the method of the present invention further comprises:
d) opening said pocket; and
e) separating the resulting opened pocket from said hardened cement.

Preferably, said cement paste in said pocket is under a pressure while said cement paste is hardening in said pocket in step c).

Preferably, the method of the present invention further comprises prior to step b):
a') disposing said pocket in a bone cavity.

Preferably, said injecting in step b) and said opening in step d) is carried out with a means which is able to be operated outside said bone cavity, and the resulting opened pocket is attached to said means.

Preferably, said separating in step e) is carried out by removing the resulting opened pocket from said bone cavity with the hardened cement remaining in said bone cavity.

Preferably, said pocket is an inflatable pocket and is made of a polymeric material. More preferably, said polymeric material is biodegradable, and said method further comprises leaving the hardened cement resulting from step c) together with the pocket in said bone cavity.

Preferably, said pocket is an inflatable pocket and is made of a polymeric material, wherein said opening in step d) comprises cutting said pocket with a blade or a thin wire. Alternatively, said inflatable pocket is made of a thin and elastic metallic material.

Preferably, said means for said injecting in step b) and said opening in step d) comprises a syringe having an injection end; a mounting mechanism at said injection end for mounting said pocket to said injection end so that an inside space of said pocket is in fluid communication only with an inside space of said syringe; a first set of wire holders on an outer surface of said syringe, which are spaced apart along a longitudinal direction of said syringe; a second set of wire holders on said outer surface of said syringe, which are spaced apart along said longitudinal direction of said syringe, wherein an imaginary plane formed by said first set of wire holders and said second set of wire holders divides the syringe into halves; and said thin wire which is slidably received said first set of wire holders and said second set of wire holders with a portion thereof passing across said injection end of said syringe. More preferably, said means further comprises a thin tube on said outer surface of said syringe along said longitudinal direction of said syringe; and said blade slidably received in said thin tube, said blade having a retractable blade and a rod connected to said retractable blade at one end thereof, so that said retractable blade received in said tube is able to protrude from said injection end of said syringe by pushing the rod, and thus said pocket can be cut by said retractable blade, and that said protruding retractable blade can be retracted by pulling the rod.

Preferably, said means for said injecting in step b) and said opening in step d) comprises a syringe having an injection end; a mounting mechanism at said injection end for mounting said pocket to said injection end so that an inside space of said pocket is in fluid communication only with an inside space of said syringe; a thin tube on an outer surface of said syringe along a longitudinal direction of said syringe; and said blade slidably received in said thin tube, said blade having a retractable blade and a rod connected to said retractable blade at one end thereof, so that said retractable blade received in said tube is able to protrude from said injection end of said syringe by pushing the rod, and thus said pocket can be cut by said retractable blade, and that said protruding retractable blade can be retracted by pulling the rod.

The present invention also discloses a device for forming a hardened cement in a bone cavity comprising a syringe having an injection end; a mounting mechanism at said injection end for mounting a pocket to said injection end so that an inside space of said pocket is in fluid communication only with an inside space of said syringe; a first set of wire holders on an outer surface of said syringe, which are spaced apart along a longitudinal direction of said syringe; a second set of wire holders on said outer surface of said syringe, which are spaced apart along said longitudinal direction of said syringe, wherein an imaginary plane formed by said first set of wire holders and said second set of wire holders divides the syringe into halves; and said thin wire which is slidably received said first set of wire holders and said second set of wire holders with a portion thereof passing across said injection end of said syringe. More preferably, said device further comprises a thin tube on said outer surface of said syringe along said longitudinal direction of said syringe; and said blade slidably received in said thin tube, said blade having a retractable blade and a rod connected to said retractable blade at one end thereof, so that said retractable blade received in said tube is able to protrude from said injection end of said syringe by pushing the rod, and thus said pocket can be cut by said retractable blade, and that said protruding retractable blade can be retracted by pulling the rod.

The present invention further discloses another device for forming a hardened cement in a bone cavity comprising a syringe having an injection end; a mounting mechanism at said injection end for mounting a pocket to said injection end so that an inside space of said pocket is in fluid communication only with an inside space of said syringe; a thin tube on an outer surface of said syringe along a longitudinal direction of said syringe; and said blade slidably received in said thin tube, said blade having a retractable blade and a rod connected to said retractable blade at one end thereof, so that said retractable blade received in said tube is able to protrude from said injection end of said syringe by pushing the rod, and thus said pocket can be cut by said retractable blade, and that said protruding retractable blade can be retracted by pulling the rod.

Preferably, said mounting mechanism comprises an annular groove formed on said outer surface of said syringe and an elastic ring having a shape and size corresponding to those of the said annular groove, so that a neck of said pocket can be clamped by said elastic ring received in said annular groove of said syringe after said injection end of said syringe being inserted into an opening of said pocket.

The present invention solves the aforesaid prior art drawbacks, because:
(1) Liquid confined in a closed region (within the "pocket"), avoid "leaking"; and
(2) Cement set within the closed pocket without contacting directly body fluid/blood, pressure can be applied/developed within the pocket, that increases largely the strength of the cement, reduces the risk of cement dispersion/disintegration, and also avoid "leaking".

Further, the present invention has an advantage of easy to keep a powder/liquid ratio of the cement paste accurate, that is important to cement properties such as setting time and strength.

DETAILED DESCRIPTION OF THE PREFERRED EMBODIMENTS

Figure 1A:
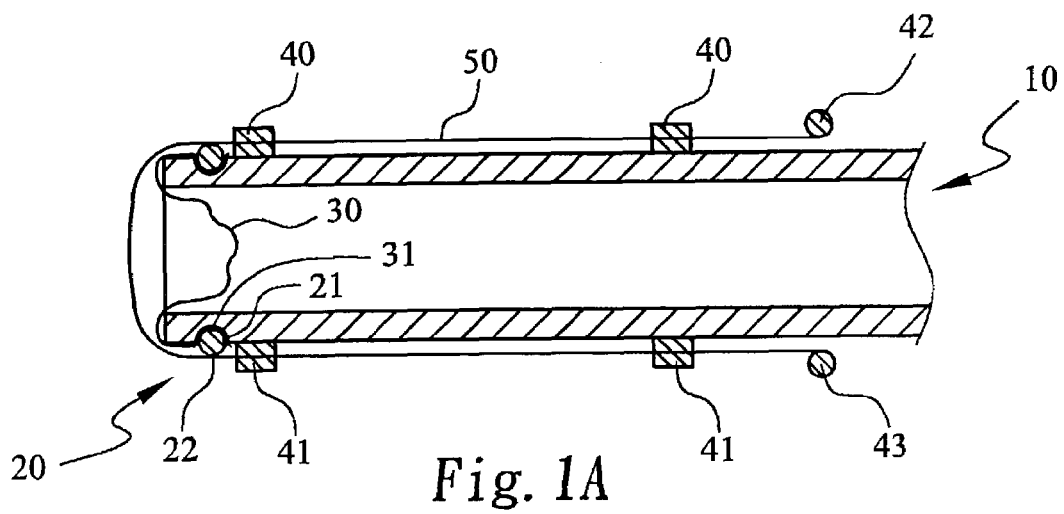
FIGS. 1A to 1E are cross-sectional views of a device for forming a hardened cement in a bone cavity constructed according to a first preferred embodiment of the present invention, and together show a process flow diagram of the method of the present invention.
Figure 1B:
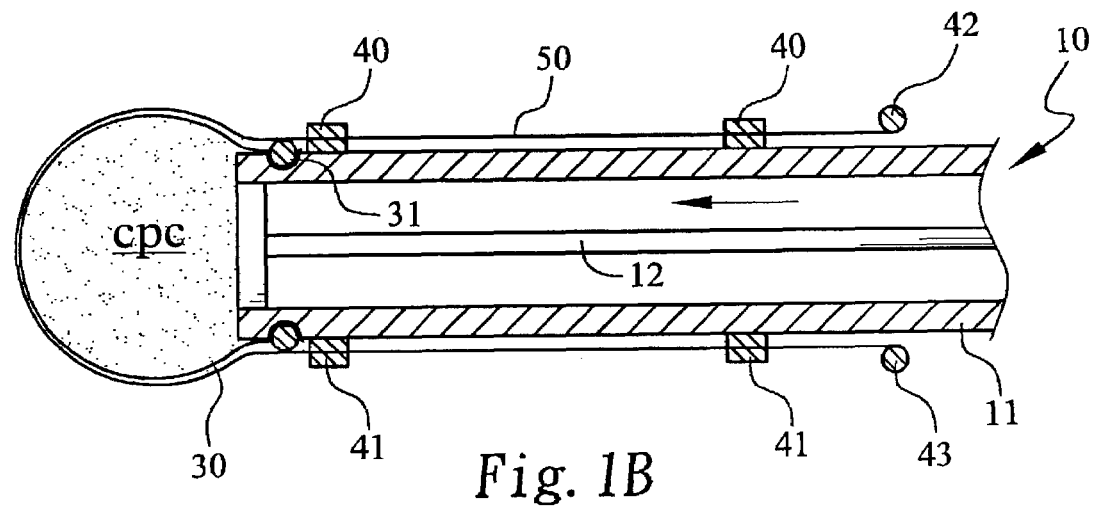

A device for forming a hardened cement in a bone cavity constructed according to a first preferred embodiment of the present invention is shown in FIGS. 1A and 1B. The device contains a syringe 10 having a substantially cylindrical tube 11 and a plug 12 slidably received in the tube 11; and a mounting mechanism 20 having an annular groove 21 provided on an outer surface of the tube 11 and near an injection end of the syringe, and a ring 22 adapted to elastically grip the annular groove 21. A pocket 30, preferably an inflatable and expandable or non-expandable pocket made of a polymeric material is used, is mounted to the injection end of the syringe by inserting the injection end into an opening of the pocket 30, so that a neck 31 of the pocket 30 covers the annular groove 21; and putting the ring 22, which is a closed ring or a C-shaped ring, on the neck 31 of the pocket 30 and clamping it at the annular groove 21 on the cylindrical tube 11.

Figure 1C:
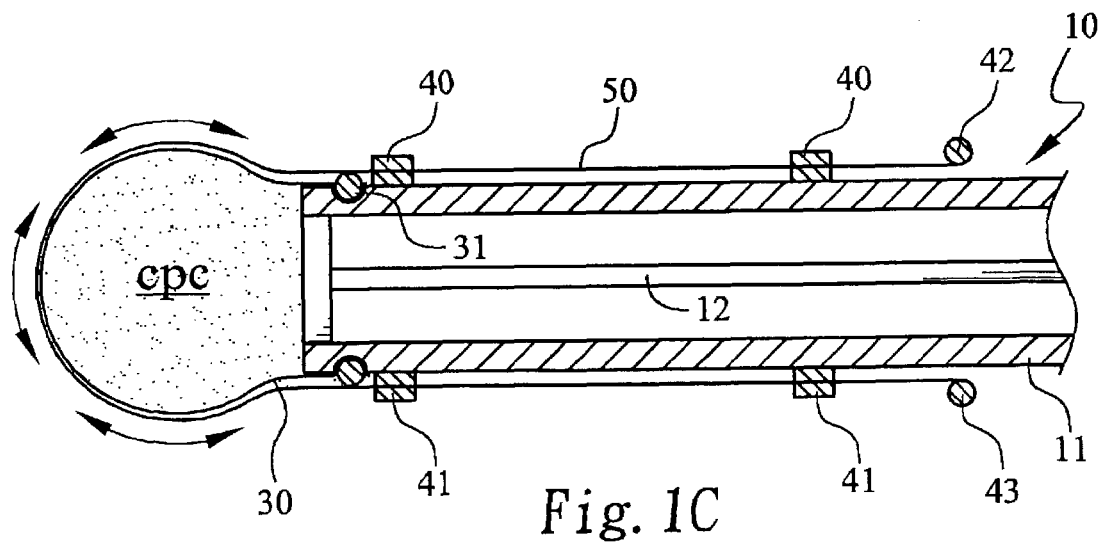
Figure 1D:
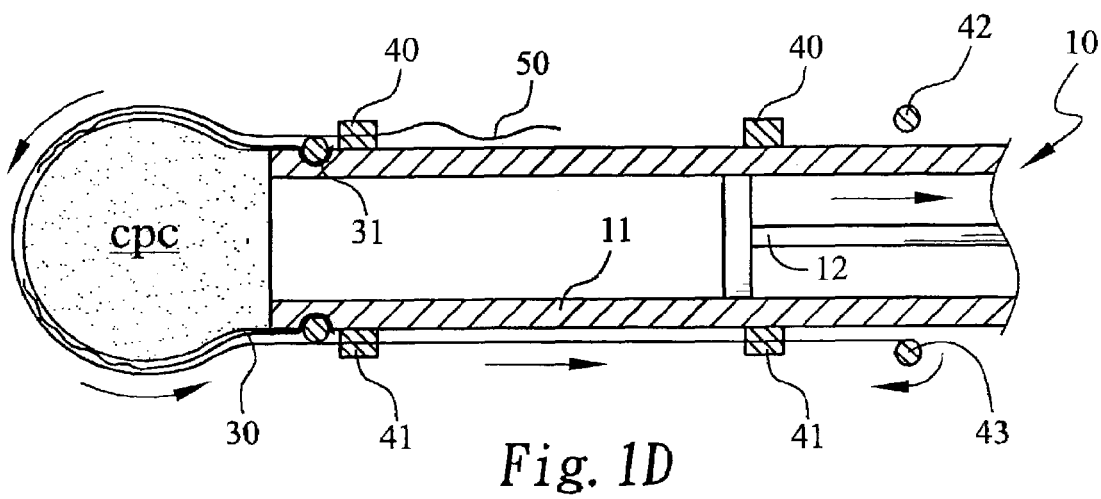
Figure 1E:
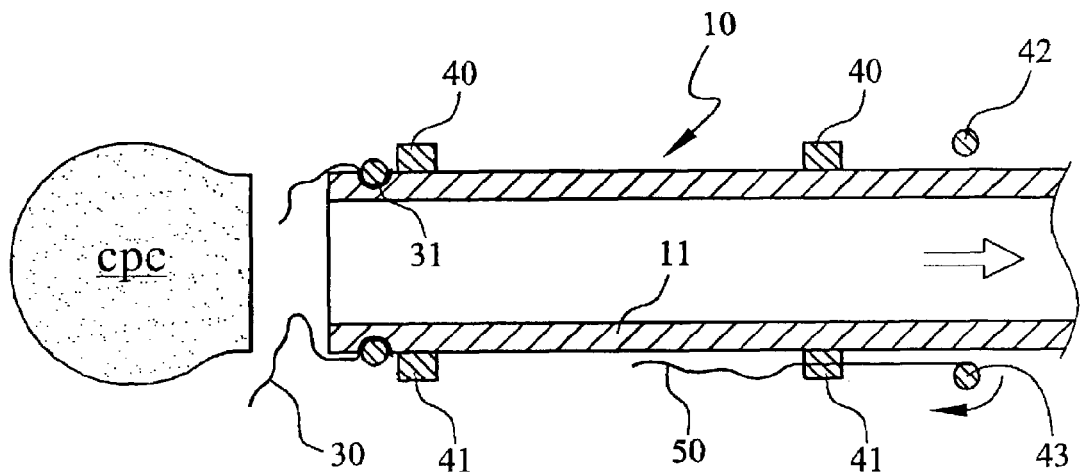

The device further contains a first set of wire holders 40 on the outer surface of the cylindrical tube 11 and along the longitudinal direction thereof; and a second set of wire holders 41 on the outer surface of the cylindrical tube 11, which are symmetrical to the first set of wire holders 40; and a thin wire 50 slidably received in the first and second sets of wire holders 40 and 41. The wire holders 40 and 41 are blocks each having a through hole, through which the thin wire 50 is passed and guided longitudinally. Preferably, the device further has two tension-adjustable rollers 42 and 43, on which the ends of the thin wire 50 are wound, so that the thin wire 50 is maintained in the first set and second set of wire holders 40 and 41 under a controlled tension. The device of the present invention is now ready to be used. The injection end of the syringe 10 is inserted into a bone cavity through an incision cut and a hole drilled by the operator. As shown in FIG. 1B, a cement paste, preferably a CPC paste giving a setting time less than 20 minutes, more preferably less than 10 minutes, is injected into the pocket 30 by pushing the plug 12 in the tube 11 toward the injection end of the syringe, so that the pocket 30 is inflated and the portion of the thin wire 50 passing across the injection end is pushed, and thus the thin wire 50 is un-wound from one or both of the rollers 42 and 43 until all the CPC paste is injected into the pocket 30. The CPC paste in the pocket 30 is maintained under the pressure exerted by the plug 12 while setting, and preferably the pressure is about 1-5000 psi, and more preferably 10-1000 psi. The thin wire 50 is pulled forward and backward alternatively at its ends under tension to cut the pocket 30 after the CPC paste is hardened in the pocket 30, as shown in FIGS. 1C-1D. One end of the thin wire 50 is released from the roller 42 by continuously pulling the thin wire 50 with the roller 43, after the pocket 30 is cut open, as shown in FIG. 1D. Finally the hardened CPC is left in the bone cavity by retreating the device together with the opened pocket 30 from the patient, as shown in FIG. 1E.

Figure 2:
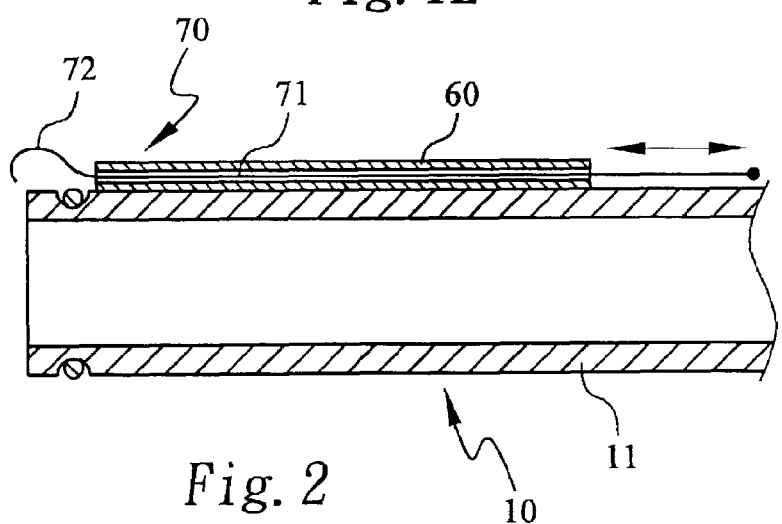
FIG. 2 is a cross-sectional view of a device for forming a hardened cement in a bone cavity constructed according to a second preferred embodiment of the present invention.

The cutting of the pocket 30 can be carried out by a different cutting structure. FIG. 2 shows a modified device of the present invention based on the design shown in FIGS. 1A-1E, wherein like elements or parts are represented by like numerals. A thin tube 60 is provided on the outer surface and along a longitudinal direction of the cylindrical tube 11 of the syringe 10. A blade 70 having a rod 71 and a retractable blade 72 is slidably received in the thin tube 60 by inserting the rod 71 into the thin tube 60 from the end near the injection end of the syringe 10 until the retractable blade 72 enters the thin tube 60. The retractable blade 72 is preferably made of metal and is elastic, so that it resumes its shape after being pushed to protrude from the thin tube 60. The operator can grip the rod 71 from the other end of the thin tube 60 to push the retractable blade 72 to protrude from the thin tube 60, cut the pocket 30 with the retractable blade 72, and retract it once again.

It is apparent that the cutting structure shown in FIG. 2 can be incorporated to the device shown in FIGS. 1A-1E to assure a successful cutting of the pocket.

Although the present invention has been described with reference to specific details of certain embodiments thereof, it is not intended that such details should be regarded as limitations upon the scope of the invention except as and to the extent that they are included in the accompanying claims. Many modifications and variations are possible in light of the above disclosure.

The invention claimed is:

1. A method for forming a hardened cement comprising the following steps:
    a) preparing a cement paste;
    a') disposing a pocket in a bone cavity;
    b) injecting said cement paste into said pocket;
    c) allowing said cement paste to harden in said pocket, wherein said cement paste in said pocket is under a pressure while said cement paste is hardening;
    d) opening said pocket; and
    e) separating the resulting opened pocket from said hardened cement;
    wherein said injecting in step b) and said opening in step d) is carried out with a means which is able to be operated outside said bone cavity, and the resulting opened pocket is attached to said means; and
    wherein said separating in step e) is carried out by removing the resulting opened pocket from said bone cavity with the hardened cement remaining in said bone cavity.

2. The method according to claim 1, wherein said pocket is an inflatable pocket and is made of a polymeric material.

3. The method according to claim 2, wherein said polymeric material is biodegradable.

4. The method according to claim 1, wherein said pocket is an inflatable pocket and is made of a polymeric material, and wherein said opening in step d) comprises cutting said pocket with a blade or a thin wire.

5. The method according to claim 4, wherein said means comprises a syringe having an injection end; a mounting mechanism at said injection end for mounting said pocket to said injection end so that an inside space of said pocket is in fluid communication only with an inside space of said syringe; a first set of wire holders on an outer surface of said syringe, which are spaced apart along a longitudinal direction of said syringe; a second set of wire holders on said outer surface of said syringe, which are spaced apart along said longitudinal direction of said syringe, wherein an imaginary plane formed by said first set of wire holders and said second set of wire holders divides the syringe into halves; and said thin wire which is slidably received by said first set of wire holders and said second set of wire holders with a portion thereof passing across said injection end of said syringe.

6. The method according to claim 5, wherein said means further comprises a thin tube on said outer surface of said syringe along said longitudinal direction of said syringe; and said blade slidably received in said thin tube, said blade having a retractable blade and a rod connected to said retractable blade at one end thereof, so that said retractable blade received in said tube is able to protrude from said injection end of said syringe by pushing the rod, and thus said pocket can be cut by said retractable blade, and that said protruding retractable blade can be retracted by pulling the rod.

7. The method according to claim 5, wherein said mounting mechanism comprises an annular groove formed on said outer surface of said syringe and an elastic ring having a shape and size corresponding to those of the said annular groove, so that a neck of said pocket can be clamped by said elastic ring received in said annular groove of said syringe after said injection end of said syringe being inserted into an opening of said pocket.

8. The method according to claim 4, wherein said means comprises a syringe having an injection end; a mounting mechanism at said injection end for mounting said pocket to said injection end so that an inside space of said pocket is in fluid communication only with an inside space of said syringe; a thin tube on an outer surface of said syringe along a longitudinal direction of said syringe; and said blade slidably received in said thin tube, said blade having a retractable blade and a rod connected to said retractable blade at one end thereof, so that said retractable blade received in said tube is able to protrude from said injection end of said syringe by pushing the rod, and thus said pocket can be cut by said retractable blade, and that said protruding retractable blade can be retracted by pulling the rod.

9. The method according to claim 8, wherein said mounting mechanism comprises an annular groove formed on said outer surface of said syringe and an elastic ring having a shape and size corresponding to those of said annular groove, so that a neck of said pocket can be clamped by said elastic ring received in said annular groove of said syringe after said injection end of said syringe being inserted into an opening of said pocket.

10. The method according to claim 1, wherein said pressure is of 1-5000 psi.

11. The method according to claim 10, wherein said pressure is of 10-1000 psi.

12. The method according to claim 1, wherein said pocket is made of a thin and elastic metallic material and wherein said opening in step d) comprises cutting said pocket with a blade or a thin wire.

* * * * *